(12) United States Patent
Axelrod et al.

(10) Patent No.: US 7,771,340 B2
(45) Date of Patent: Aug. 10, 2010

(54) METHOD AND APPARATUS FOR MODIFYING DISTANCE FROM A BRACHYTHERAPY RADIATION SOURCE TO SENSITIVE ANATOMICAL STRUCTURES

(75) Inventors: Steve Axelrod, Los Altos, CA (US); James E. Jervis, Atherton, CA (US); Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 0 days.

(21) Appl. No.: 11/881,835

(22) Filed: Jul. 28, 2007

(65) Prior Publication Data

US 2009/0030258 A1 Jan. 29, 2009

(51) Int. Cl.
*A61N 5/00* (2006.01)
(52) U.S. Cl. ........................................................ 600/3
(58) Field of Classification Search .................. 600/1–8
See application file for complete search history.

(56) References Cited

U.S. PATENT DOCUMENTS

| | | | |
|---|---|---|---|
| 3,872,856 A | 3/1975 | Clayton | |
| 5,308,356 A | 5/1994 | Blackshear, Jr. et al. | |
| 5,653,683 A | 8/1997 | D'Andrea | |
| 5,720,717 A | 2/1998 | D'Andrea | |
| 5,947,891 A | 9/1999 | Morrison | |
| 6,413,204 B1 | 7/2002 | Winkler et al. | |
| 6,491,619 B1 * | 12/2002 | Trauthen et al. | 600/3 |
| 6,652,441 B2 * | 11/2003 | Weinberger et al. | 600/3 |
| 6,673,006 B2 | 1/2004 | Winkler | |
| 6,746,465 B2 | 6/2004 | Diederich et al. | |
| 6,752,752 B2 | 6/2004 | Geitz | |
| 6,923,754 B2 | 8/2005 | Lubock | |
| 6,955,641 B2 | 10/2005 | Lubock | |
| 7,494,456 B2 * | 2/2009 | Stubbs et al. | 600/3 |
| 7,534,202 B2 | 5/2009 | Eng | |
| 2005/0080313 A1 * | 4/2005 | Stewart et al. | 600/3 |
| 2005/0085681 A1 | 4/2005 | Stubbs et al. | |
| 2005/0101860 A1 | 5/2005 | Patrick et al. | |
| 2006/0173235 A1 | 8/2006 | Lim et al. | |
| 2007/0167666 A1 | 7/2007 | Lubock et al. | |
| 2007/0167667 A1 | 7/2007 | Lubock et al. | |

* cited by examiner

*Primary Examiner*—Charles A Marmor, II
*Assistant Examiner*—Christine D Hopkins
(74) *Attorney, Agent, or Firm*—Thomas M. Freiburger

(57) ABSTRACT

A balloon brachytherapy applicator has either a single or double chambers, with the capability of "blistering" outwardly at a specified area on one side of the balloon. This is useful to move sensitive tissue farther away from a radiation source within a source guide inside the balloon. In one case a secondary compartment is formed on the primary balloon, and is separately inflatable so as to allow blistering as desired when needed. In another form the balloon comprises a single chamber but with a "window" or area in which the balloon wall is elastic, or substantially more elastic than the main balloon wall, so that inflation of the balloon up to a certain point forms a substantially regular balloon shape, and the addition of further pressure will blister out the elastic area to increase the distance between the shaft and the sensitive tissue in a desired orientation of the balloon.

1 Claim, 5 Drawing Sheets

METHOD AND APPARATUS FOR MODIFYING DISTANCE FROM A BRACHYTHERAPY RADIATION SOURCE TO SENSITIVE ANATOMICAL STRUCTURES

BACKGROUND OF THE INVENTION

This invention concerns radiation therapy, especially brachytherapy, for treating tissues which may have diffuse proliferative disease.

In brachytherapy, the radiation source is generally placed within a surgically created or naturally occurring cavity in the body. In particular, this invention relates to delivery of radiation therapy to tissue as might be found in the human breast, or to other tissue, often following surgical treatment of cancer.

Radiation therapy following tumor resection or partial resection is generally administered over a period of time in partial doses, or fractions, the sum of which comprises a total prescribed dose. This fractional application takes advantage of cell recovery differences between normal and cancerous tissue whereby normal tissue tends to recover between fractions, while cancerous tissue tends not to recover.

In brachytherapy, a prescribed dose is selected by the therapist to be administered to a volume of tissue (the target tissue) lying outside the treatment cavity into which the radiation source will be placed. Generally the prescribed dose will include a minimum dose to be delivered at a preferred depth outside the treatment cavity (the prescription depth or point). Since, in accordance with the laws of physics, radiation intensity falls off sharply with increasing distance from the radiation source, especially from the very near regions outwardly, it is desirable to create and maintain a space between the source of radiation and the first tissue surface to be treated (generally the cavity wall since the source is placed within the cavity) in order to moderate the absorbed dose at the cavity surface. This is often done by placing a balloon or other applicator in the cavity with the radiation source inside the applicator. Such balloons are preferably inflated with a fluid which is substantially water and since water is similar to soft tissue with respect to radiation attenuation, this simplifies prescription planning.

Often the prescription depth outside the cavity is to be uniform. In this isotropic case, it is therefore important that the incident radiation on the interior surface of the cavity be the same at all points being treated. Depending on the emission pattern of the source being used, it may be necessary to sequentially position a single radiation source through a series of positions, often within a source channel or guide tube positioned on an axis of symmetry of the applicator balloon (or utilize other positions or multiple sources strategically placed) to produce the desired uniformity in the aggregate. Furthermore, by selecting the radiation source intensity (radioisotope emissions or x-ray tube output) and controlling treatment time and the distance from the source(s) to the cavity interior surface, the incident radiation can be sufficiently moderated to avoid substantial damage to normal tissue.

In contrast to the isotropic situation just described, the treatment cavity may be near sensitive tissue structures, e.g., skin, such that an isotropic prescription plan may include points which intersect or encompass such structures. In such a situation, the therapist may be forced to locally shield emitted radiation from within the treatment cavity (see co-pending application Ser. No. 11/471,277 incorporated by reference herein in its entirety), or to resort to radiation sources which emit anisotropically. Such capabilities may not be readily available or practical. In such cases, and there are many, the patient may therefore be denied the advantages of brachytherapy.

One accepted standard in radiation therapy for the range of applicators currently in use is that a one centimeter prescription depth of tissue outside the treatment cavity be used for dose planning. Assuming the tissue at the prescription depth receives the desired dose, the tissue nearest the source should not receive more than 2.5 to 3 times the prescription dose. Standards also usually require that the skin not receive a dose of more than 1.5 times the prescription dose. With a one centimeter prescription depth, the balloon diameter must be about 2.7 to 3.4 cm diameter to meet the above near-tissue standard, and this usually requires the skin be at least 6-8 mm out from the surface of a balloon applicator engaged against the tissue in a cavity. A distance of less than about 6-8 mm may result in doses higher than 1.5 times the prescription dose which are known often to result in undesirable cosmesis. This problem commonly arises after a lumpectomy and is a counter-indication for isotropic brachytherapy. In order to make brachytherapy available to more patients having resection cavities in close proximity to skin surfaces or to other radiation sensitive structures, the apparatus and/or methods of this invention may be employed.

SUMMARY OF THE INVENTION

The balloons of the applicators of this invention are similar to those of existing applicators being axially symmetrical, facilitating positioning of the radiation source along the balloon axis, and which produce or tend to produce a desired cavity shape for isotropic brachytherapy upon inflation. In addition, however, the applicators of this invention may comprise at least one secondary balloon, preferably attached to a portion of the surface of the primary balloon in a manner wherein a substantial portion, often half of the secondary balloon surface (before inflation), is shared in common with the portion of the primary balloon surface to which it is attached, appearing in a form not unlike a blister. An alternate applicator system might comprise two (or more) independent balloons positioned to create the same spatial arrangement. Still another embodiment has a single balloon, but with a patch or area on one side that is substantially more flexibly elastic than the remaining balloon wall, so that once the balloon is fully inflated to a regular shape, further pressure can be added to blister out the flexible area.

There are several types of balloons which can be used for brachytherapy. One extreme is an inelastic balloon which might be of polyester or polyethylene terephthalate (PET) with an inflated shape like the shape desired for the cavity during brachytherapy. On inflation, such balloons exhibit a sharp inflation pressure rise as the desired shape is attained. Properly designed, these balloons are relatively hard when properly inflated and are capable of forcibly conforming or tending to conform a body cavity in soft tissue into the desired shape, i.e. the balloon shape. At the opposite extreme are elastic balloons which, on inflation, tend to conform themselves to the cavity in which they are placed. If inflated sufficiently, such an elastic balloon may tend to enlarge the cavity overall in keeping with the mechanical resistance of the tissue it encounters, but in general it is so weak as to be incapable of producing predetermined features in the cavity or its surface with any degree of accuracy. Such balloons might be made from thin sections of silicone elastomers, for example.

Inelastic/elastic behavior is not only a matter of material choice, but also of design parameters. For example, by varying balloon wall thickness, a balloon can be produced which is useful over at least a limited inflation range, and which exhibits a desired degree of inelastic or elastic behavior as might be appropriate to the application. Between the extremes described above are a multitude of material and design options which can be used to fabricate useful applicator balloons with intermediate properties. Such fabrication may include dip forming or injection molding. It can also include fabrication by bonding or welding sheet material which can subsequently be inflated in free air or in molds such that desired shapes result, and when reinflated within a tissue cavity, will substantially reproduce their desired shape. Heat may also be useful in creating desired, reproducible shapes. These and other methods are well known to those of skill in the art of balloon fabrication.

As described above, brachytherapy situations often arise in which the range of target tissue includes sensitive structures which might be at risk if subjected to a prescription dose or greater. In a preferred embodiment, a secondary balloon on the surface of the primary balloon may be oriented toward the at-risk structure when the applicator is placed within the body cavity. As the primary balloon is inflated, the orientation of the secondary balloon is maintained such that after completion of primary inflation which generally shapes the body cavity for brachytherapy, the secondary balloon may be inflated, increasing the distance locally between the radiation source in its guide tube and the at-risk structure. If inflation of the secondary balloon is carried to an extreme, at least in soft tissue, the prescription points adjacent to such structure would actually be brought into the secondary balloon volume. In practice, however, it is preferred that inflation of the secondary balloon only proceed until the at-risk structure is within safe radiation limits such that intervening tissue nearer the source receive as much dose as possible—ideally between the full and 2.5-3 times the full prescription dose, the latter at the cavity surface. As stated previously, the preferred inflation fluid in both balloons should have the radiation attenuation characteristics of water so as to simplify dose planning.

It is important that inflation of the secondary balloon not create air voids between the applicator and cavity near the creases or boundaries where the secondary balloon attaches to the primary balloon. Any such tendency to voids can be mitigated by use of secondary balloons that are more elastic relative to the more inelastic behavior of the primary balloon. Alternatively, surface channels and suction through suction lumina can be used to both eliminate voids between the cavity and balloons and withdraw seroma or other fluids. Generally, it is also important that the inflation pressure within the primary balloon be sufficient to prevent the common portion of the balloon surfaces from substantial intrusion into the interior space of the primary balloon as the secondary balloon is inflated. In an alternative method, however, the degrees of inflation may be balanced such that the intrusion of the secondary balloon into the volume of the primary balloon is substantial, perhaps even sufficient to displace the radiation source guide tube at the center of the primary balloon. This too would have the effect of increasing the distance from the source to the at-risk structure, but by bending the guide tube, the dose planning process may become more complicated.

A different embodiment comprising two adjacent balloons sharing a common interface could be used similarly. In this embodiment, two adjacent balloons share a common interface film or barrier, the film containing or attached to and supporting the guide tube for the radiation source. By adjusting the inflation between the two balloons, the volumes can be adjusted to (1) fill the cavity, (2) protect the at-risk structure(s) from overdose exposure, and (3) maintain adequate distance opposite the at-risk structure to avoid overdosing the opposing cavity surface. With this approach, however, the dose planning again may need to accommodate a curved source path, as with the previous variation.

In the embodiments described above, it is assumed that the inflation circuits of the primary and (if more than one) secondary balloon are independent. In some circumstances, they might have circuits in common. Further, one aspect of the invention encompasses a balloon of inelastic material but with a patch or area of elastic material, fairly stiff, that will begin to inflate (blister out) only after the main (inelastic) balloon walls are fully expanded. Additional pressure will cause the elastic area to bulge out, to the desired degree.

However, another and perhaps more straightforward approach to protecting at-risk structures may be to create single-balloon applicators having sections with different isodose emission characteristics, rather than complex balloons. Balloon radiation attenuation properties (or radio-opacity) can be varied by addition of barium or bismuth compounds, attenuating fillers (e.g. tungsten powder) or by other methods known in the art, and in addition to providing attenuation are also useful for the dose planning process. Applicators with partially radio-opaque balloons are useful for another purpose as well: conventional imaging, for example by x-ray, can be used to locate the balloon elements of the applicator, and hence orient the balloon in relation to anatomical structures.

The terms "blistering balloon" and "blister" and "blister portion" of a balloon are intended to encompass multiple balloons or a multi-chambered balloon or a single balloon with a blister portion, all being effective to blister out in one area for the purpose described.

Optionally, radiation sensors can be mounted on and incorporated into applicators of this invention as well as placed in or on the patient's anatomy to locate or ascertain the orientation of the applicator, to verify dose delivery and/or to control the radiation source during the brachytherapy treatment. For example, output from a sensor or sensors placed on the surface of the secondary balloon adjacent the at-risk structure would indicate the range to the source and assure protection of the structure. Sensors can also be employed during the treatment planning process to take curvature of the source guide tube into account and adjusting the positions and dwell times comprising the fractional treatments to be delivered accordingly. Using feedback, sensor output can be used to fine-tune treatment parameters between fractions or in real time. Such sensors may also be used to indicate spatial positioning of the source relative to other structures. For example, output from a sensor or sensors placed on the surface of the secondary balloon adjacent the at-risk structure would indicate the range to the source (of known output and stability characteristics) and assure protection of the structure. Sensors can also be employed during the treatment planning process to take curvature of the source guide tube into account and to adjust the positions and dwell times comprising the fractional treatments to be delivered accordingly. Such sensors can communicate by conventional wiring or by wireless means with monitors, controllers or other apparatus located outside the patient's body. An alternate, and perhaps more accurate method of determining spatial positioning between elements of the brachytherapy apparatus and anatomical structures is by use of eddy-current ranging. By positioning conductive targets on applicator balloon elements which can follow balloon distension during inflation and inserting a wand into the source channel to generate an RF field, the distance from the wand to the target may be determined with accuracy. This information, combined with other azimuthal or directional imaging information, can be used in dose planning to assure at-risk structures within the body are protected. Suitable targets would include aluminum or silver chips on balloon element surfaces, perhaps in wavy patterns to accommodate surface distortion (in the case of a substantially inelastic balloon) or surface expansion (in the case of a substantially elastic balloon). Silk-screen printing on the balloon elements is one method by which such targets might be provided, and other methods would be apparent to those of skill in the art. Such eddy current sensing methods and apparatus can be obtained from Kaman Measuring Systems Corp., Middletown, Conn. and others.

Although the embodiments described above assume only one secondary balloon, the principles described above may be used to fashion applicators which can be used to protect one or more sensitive structures with multiple secondary balloons during administration of brachytherapy without unduly complicating the dose planning process, thus making brachytherapy a viable treatment option where it would not be with traditional applicators. Furthermore, by judicious choice of direction in which the applicator is inserted into the treatment cavity, a wide variety of complex structure situations can be accommodated with only a few applicator models having one, or at most two secondary balloons. An applicator with two secondary balloons might be used, for example, to protect bone adjacent one side and skin adjacent another side.

These and other objects, advantages and features of the invention will be apparent from the following description of preferred embodiments, considered along with the accompanying drawings.

DESCRIPTION OF PREFERRED EMBODIMENTS

Figure 1:
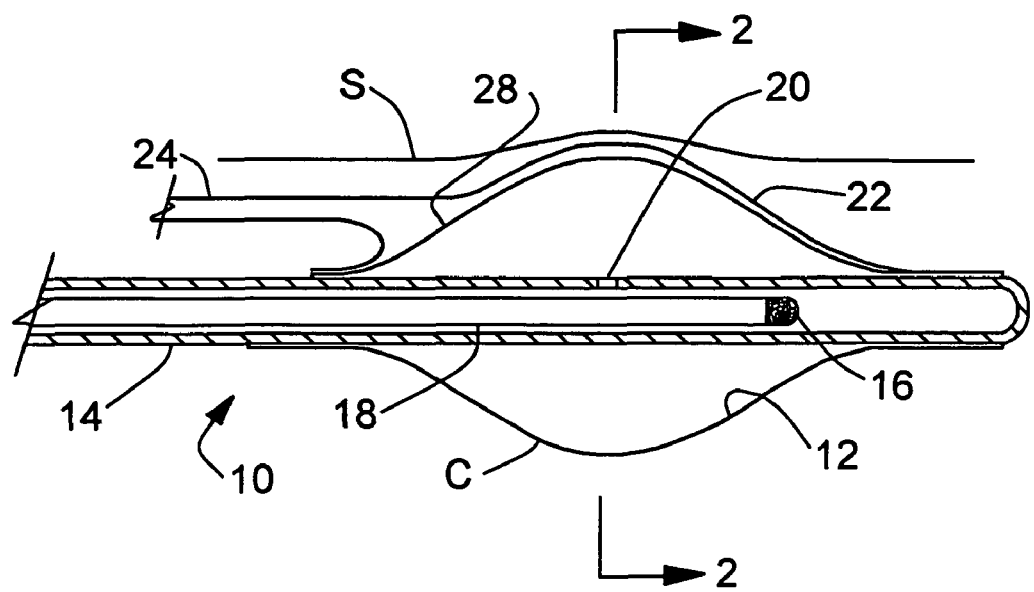
FIG. 1 depicts in longitudinal schematic section, an applicator and radiation source in a treatment cavity and having a primary balloon (inflated) and a secondary balloon (uninflated) positioned on one side. The patient's skin is shown near the resection cavity closely adjacent to the secondary balloon.

In the drawing figures and the descriptions which follow, the balloons of the applicator embodiment are shown and described schematically in that balloon walls and membranes are generally represented by one line. It is preferable that the balloons be inflated with water or water-like liquid as described above. In addition to simplifying dose planning, control of inflated shapes can be substantially obtained by filling each chamber to a specified volume. Alternatively, however, inflation can be by gaseous medium with the desired shape control obtained by pressure control, perhaps verified by conventional imaging techniques, including x-ray where the balloon element materials are doped with radio-opaque fillers like barium sulfate or bismuth bicarbonate to enhance their display on x-ray film.

FIG. 1 schematically shows in section, an applicator 10 having a primary balloon 12 with a concentric radiation source guide tube 14 having a radiation source 16 inside, mounted on the end of a source catheter 18, all positioned within a treatment cavity C. The guide tube further comprises an inflation port 20 into the primary balloon connecting with the annular passage within the guide tube 14 and outside of the catheter 18. The primary balloon is shown inflated. A deflated secondary balloon 22 having an independent inflation circuit 24 is shown to one side of the primary balloon 12, sharing a common portion 28 of balloon wall with the primary balloon 12. The patient's skin S is shown closely adjacent to the secondary balloon 22. For purposes of this discussion, the distance between the source and skin is presumed to be inadequate for brachytherapy, for the prescription to be applied.

Figure 2:
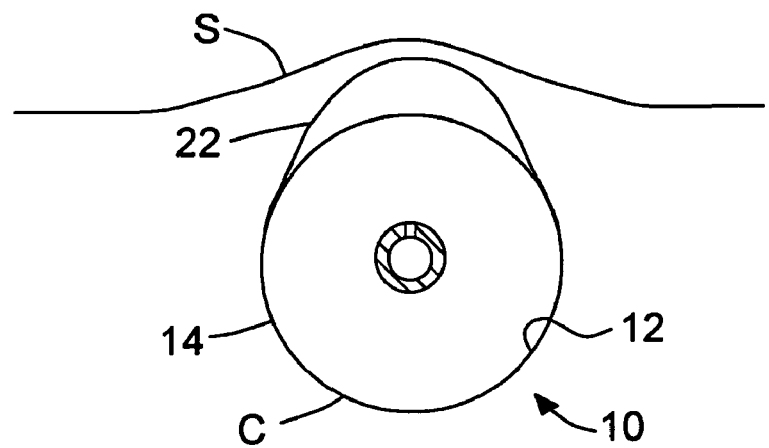
FIG. 2 depicts the balloon structure and source of FIG. 1 in transverse schematic section as indicated by the line 2-2 in FIG. 1 in the cavity with both balloons inflated and the skin lifted, increasing the source-to-skin distance.

Once the applicator is positioned with the secondary balloon oriented toward the skin where the source-to-skin distance needs to be increased, the primary balloon is inflated. The secondary balloon 22 is subsequently inflated, increasing the source-to-skin distance locally as shown in FIG. 2, to a safe distance for the radiation to be applied while still treating the tissue 29 between the cavity C and the skin S. To avoid trapped air within the balloons, it may be desirable to evacuate the balloons before inflation.

Figure 3A:
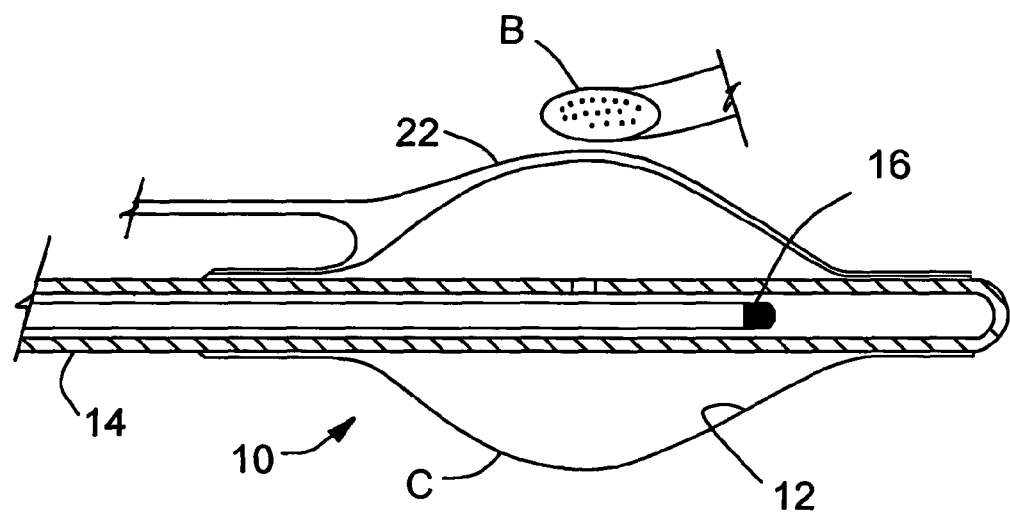
FIG. 3A depicts in longitudinal schematic section an applicator and source similar to that of FIG. 1, again with the primary balloon inflated and the secondary balloon uninflated, but placed near a bone within the patient's anatomy.

FIG. 3A shows a situation similar to that of FIG. 1, but where the structure to be protected from over treatment is a more rigid section of bone B rather than the skin S of FIG. 1. The objective in FIG. 3A is to increase the source-to-bone distance and is similar to the purpose of FIG. 1. However, since the bone is a more solid structure than the skin, the distance is mainly increased by moving the source 16, source guide tube 14, and to an extent moving and reshaping the treatment cavity C as a whole away from the bone B, by inflating the secondary balloon 22, as illustrated in FIG. 3B.

Figure 3B:
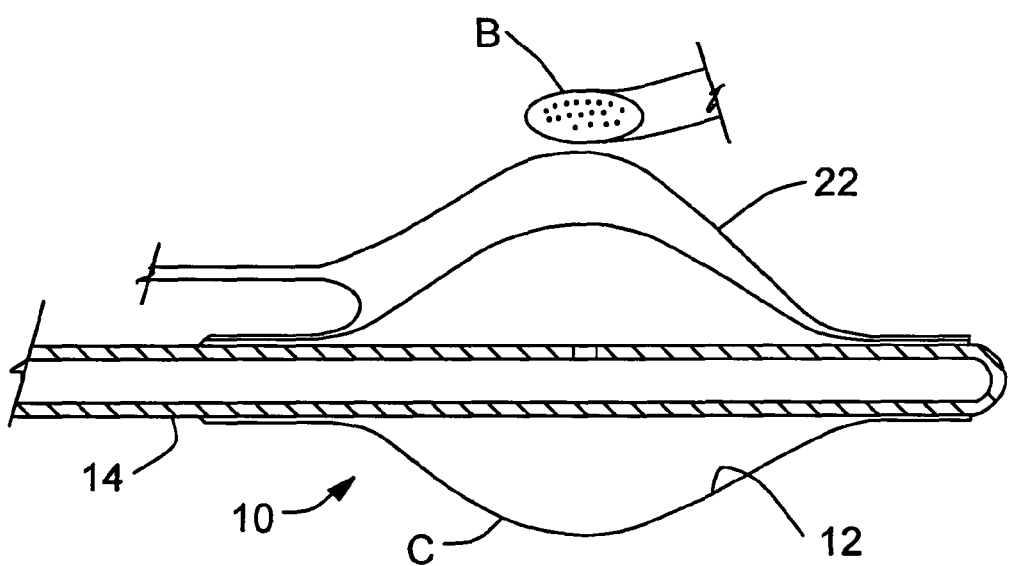
FIG. 3B is a view similar to FIG. 3A but with both balloons inflated such that the treatment cavity is pushed away from the bone, increasing the source-to-bone distance.
Figure 4:
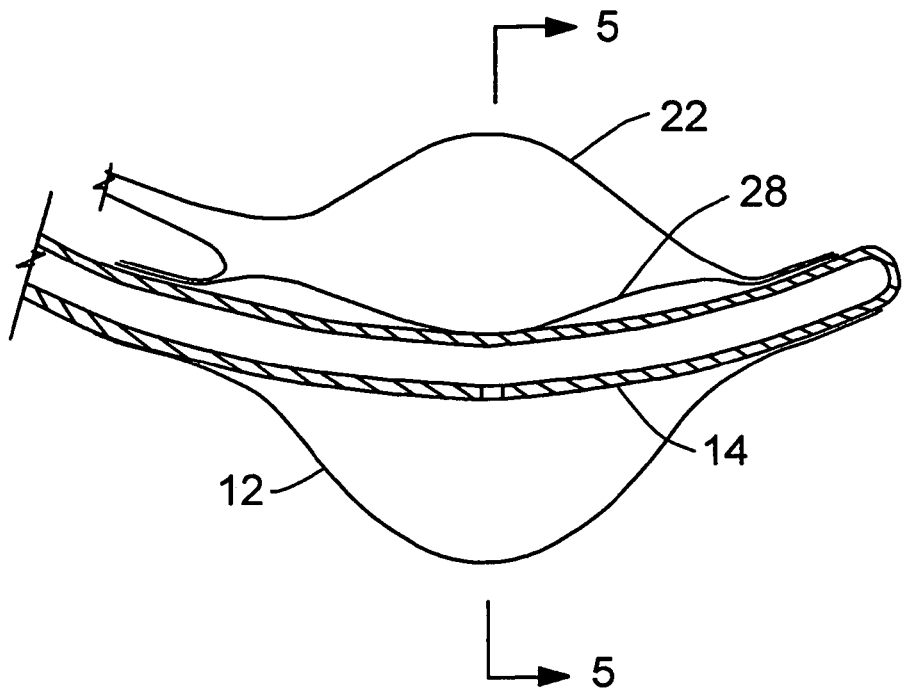
FIG. 4 is another similar view of an applicator with both balloons inflated. The secondary balloon is inflated relative to the first sufficiently to cause the common membrane between to deflect into the primary balloon volume causing deflection of the source guide tube.
Figure 5:
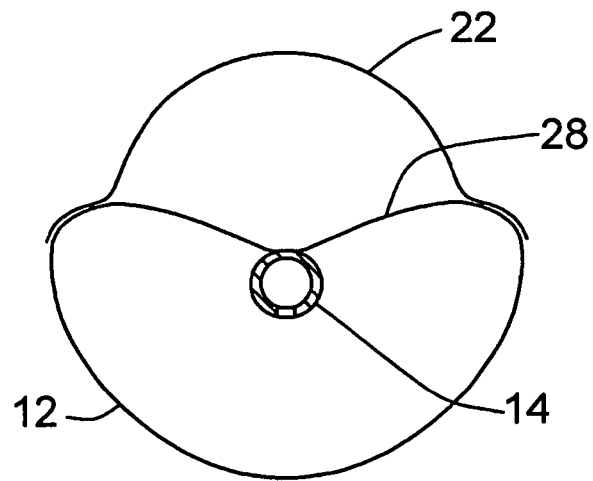
FIG. 5 is a transverse section view along the line 5-5 in FIG. 4, showing the applicator of FIG. 4 with both balloons inflated.

FIG. 4 is an extension of the action described in FIGS. 3A and 3B wherein the inflation between the primary and secondary balloons is balanced in a manner wherein inflation of the secondary balloon 22 causes the common wall 28 between the balloons to intrude into the volume of the primary balloon 12 until it contacts and displaces the source guide tube 14 away from the outer surface 26 of the secondary balloon 22. This causes bending of the source guide tube 14 as shown in FIG. 4. This action is shown in transverse section in FIG. 5 as seen at the plane 5-5 in FIG. 4.

Figure 6A:
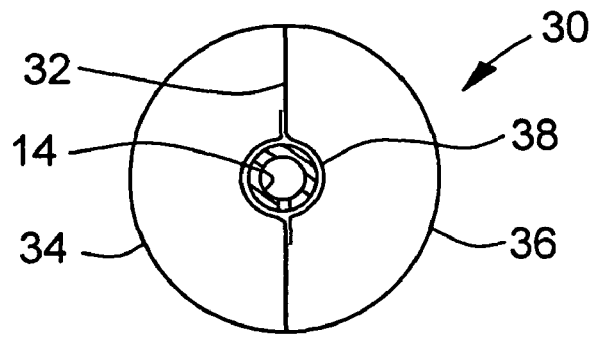
FIG. 6A shows in schematic transverse section, a two chambered applicator having a central membrane that includes a source guide tube. Both chambers are shown inflated in a balanced manner.
Figure 6B:
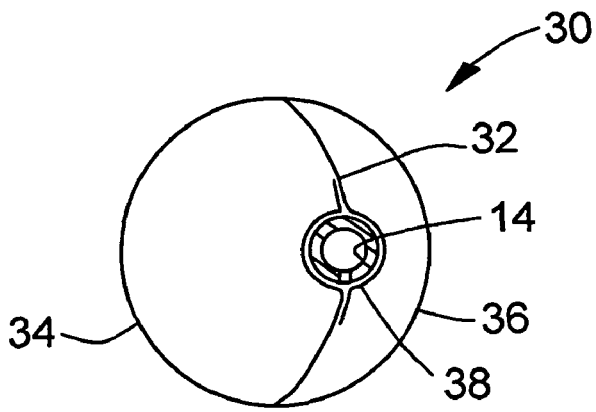
FIG. 6B is a similar section view showing the applicator of FIG. 6A with the inflation unbalanced so as to move the guide tube to the right.
Figure 6C:
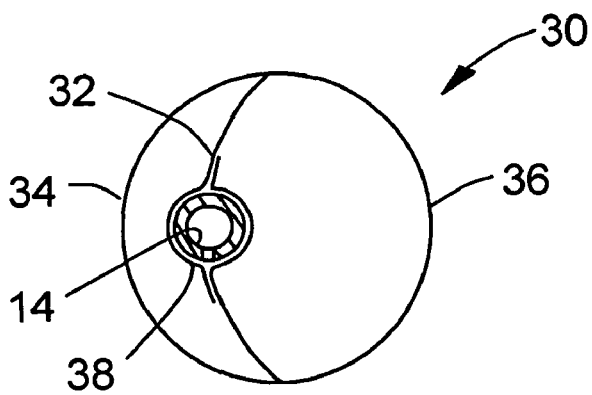
FIG. 6C is another similar section showing the applicator of FIG. 6A with the inflation balanced in a manner to move the guide tube to the left.

FIG. 6A shows a balloon applicator 30 having a central wall or membrane 32 positioned between two juxtaposed balloons, a left balloon 34 and a right balloon 36. The inflation of balloons 34 and 36 is shown balanced. The central wall 32 can be a common wall comprising a single layer, or it can be two layers, each balloon having its own contiguous wall. In either event this central wall can be referred to as a common wall. A source guide tube 14 is shown centrally positioned on or along the wall 32 in a pocket 38 and bonded in place using conventional methods. Unbalancing the inflation between the balloons 34 and 36 causes a displacement of the central wall 32 and the guide tube 14. As shown in FIG. 6B, if the inflation of the left balloon 34 exceeds that in right balloon 36, the central wall 32 is displaced to the right as shown in FIG. 6B. If the inflation differential is reversed, the central wall is displaced to the left as shown in FIG. 6C.

The source guide tube 14 preferably is bonded to the pocket 38 in the central wall 32 of the applicator 30, but alternatively, the guide tube 14 need not be bonded to the central wall, and can be temporarily inserted during radiotherapy.

Figure 7:
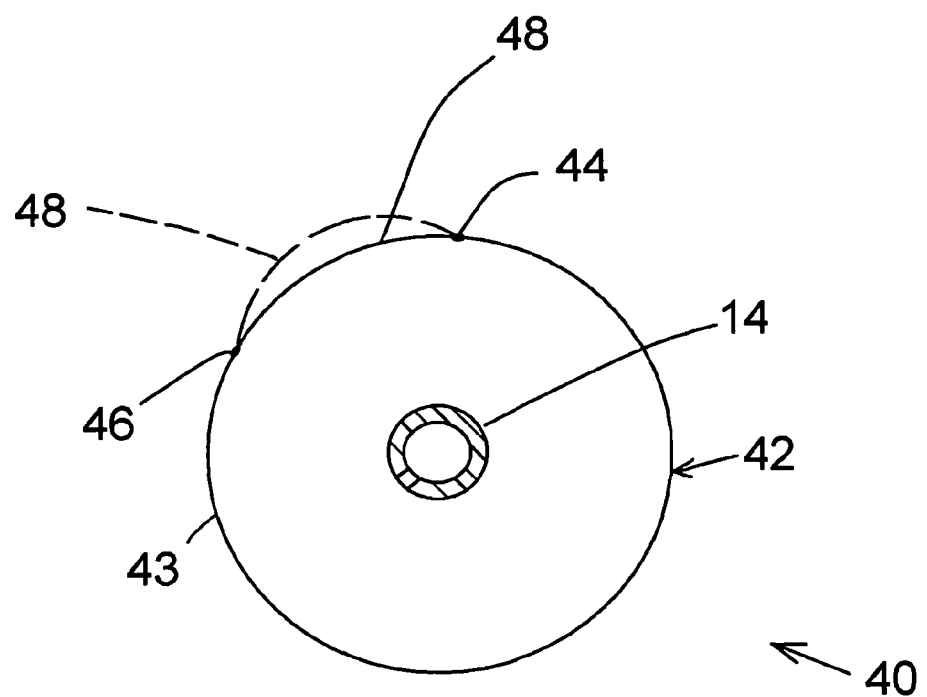
FIG. 7 is a transverse sectional view showing another embodiment wherein the applicator has a single balloon with a wall area that is expandable as a "blister".

FIG. 7 shows another embodiment of the invention, in this case an applicator 40 with a source guide 14 and a single balloon 42 secured on the shaft comprising the source guide. Here, the single balloon 42 is substantially inelastic throughout most of its surface, the majority of the balloon from the boundary line 44 to the boundary line 46 (seen as points in the sectional view of FIG. 7). An elastic balloon area is shown at 48, sealed or bonded in an appropriate manner to the majority inelastic portion 43 of the balloon, the shape of this area 48 preferably being approximately circular or elliptical and forming generally a portion of a sphere when the balloon 42 is inflated just to the point of fully expanding the balloon. The elastic portion 48 is fairly stiff so that this area 48 substantially conforms to and extends the generally spherical (or other) shape of the balloon up to the point when the inelastic portion is fully expanded. However, further pressure, deliberately admitted to the balloon, will "blister" out this elastic balloon portion 48, to form a bulge or blister as shown in dashed lines in the drawing. With this elastic portion 48 correctly oriented toward the region where the skin or the sensitive tissue may be too close to the radiation source during brachytherapy treatment, the balloon's "blister" portion 48 can be used to increase the distance from the source to the sensitive tissue, without requiring multiple inflation chambers.

The balloon elements described above can be molded by conventional methods, injection molding, blow molding, pressure forming or the like, and bonded to form the configurations described. By adjusting wall thicknesses and material properties, various degrees of elasticity can be obtained, and in fact elasticity can be varied between balloon elements of an applicator, or even between adjacent portions of the same element.

The applicators of this invention can also be fabricated by welding sheet stock components to fashion the desired elements. Generally speaking, thicker sheet elements will act more inelastically than thinner elements. One preferred material for welded fabrication is polyurethane film, such as that of Deerfield Urethane, Inc., South Deerfield, Mass. These films can be welded together using hot-wire or other techniques. Two (or more) film layers are pressed together between release sheets (for example of Teflon coated fabric) and resilient platens and heated locally by wireforms of conventional heater wire, for example, Nichrome wire. Such wireforms may be fastened to one or both of the release sheets using high-temperature tape and powered by a Variac (ISE, Inc., Cleveland, Ohio) adjusted to produce desirable, but essentially two-dimensional welded shapes. The assemblies may then be inflated, preferably with air, to desired three-dimensional shapes and heat-treated to set their "at-rest" configuration. The transition to three dimensional shapes may require trial and error to achieve the desired result. Varying film thicknesses, exaggerating two-dimensional shapes, preforming elements for later welding and use of forming molds are all techniques which can be used to achieve the desired results. Those of skill in polymer fabrication can quickly achieve the results necessary. A useful range of stock applicators will include several sizes, each with one or more secondary balloons. Some secondary balloons would be generally elongate and have an orientation transverse to the guide tube axis; others would have a long axis parallel to the guide tube axis.

In use, once the therapist determines that radiation sensitive structures lie within or closely adjacent to the target tissue, the planning process proceeds as in isotropic brachytherapy planning, but anticipates use of applicators having space adjustment capabilities in keeping with those of this invention. After selection of the most convenient size, shape and secondary features, the directional orientation for insertion of the applicator into the cavity can be chosen, and insertion into the cavity completed. The balloons are then inflated. Using eddy current sensing methods and apparatus (for example, that from Kaman Measuring Systems Corp., Middletown, Conn.) and/or imaging as described previously, or on-board radiation sensor input (with low dose sampling of delivered radiation intensity) the distances from source positions to pertinent anatomical structures can be determined, and source positioning and dwell times can be optimized to produce the prescribed therapy. Radiotherapy can then commence.

The above described preferred embodiments are intended to illustrate the principles of the invention, but not to limit its scope. Other embodiments and variations to these embodiments will be apparent to those skilled in the art and may be made without departing from the spirit and scope of the invention as defined in the following claims.

We claim:

1. An applicator with a balloon for brachytherapy radiation treatment, comprising:

an applicator shaft for extending into a body cavity or space, including an internal lumen in the shaft for receiving a radiation source, a primary balloon fixed exteriorly to the shaft, and including an inflation lumen connected to an internal inflatable volume of the primary balloon and extending to a proximal region of the applicator, a secondary balloon secured along one wall to the primary balloon and separately inflatable, with an inflation channel connected to an internal inflatable volume of the secondary balloon and extending to a proximal region of the applicator, and wherein the primary balloon and the secondary balloon comprise left and right balloons of generally equal size, sharing a common central wall between the left and right balloons, with the applicator shaft positioned in a pocket in the common central wall, whereby inflation of the left and right balloons can be deliberately unbalanced to cause a displacement of the central wall and the shaft carrying a radiation source, in order to move the source farther from skin or other sensitive tissue, whereby the primary balloon can be inflated after the applicator is inserted into a body cavity or space, and, if the skin or another organ or sensitive tissue is too close to the primary balloon when inflated such that prescribed radiation from the radiation source could damage the skin or other sensitive tissue, the secondary balloon can be inflated to an extent as needed to increase the distance between the radiation source and the skin or other tissue.

* * * * *